(12) United States Patent
Kuo et al.

(10) Patent No.: US 11,918,435 B2
(45) Date of Patent: Mar. 5, 2024

(54) METHOD OF PRODUCING ADAPTIVE ELEMENT FOR DENTAL IMPLANTATION

(71) Applicants: Hsin-Yu Kuo, New Taipei (TW); Tsung-Fu Hung, New Taipei (TW); Po-Jan Kuo, New Taipei (TW)

(72) Inventors: Hsin-Yu Kuo, New Taipei (TW); Tsung-Fu Hung, New Taipei (TW); Po-Jan Kuo, New Taipei (TW)

(*) Notice: Subject to any disclaimer, the term of this patent is extended or adjusted under 35 U.S.C. 154(b) by 0 days.

(21) Appl. No.: 17/322,638

(22) Filed: May 17, 2021

(65) Prior Publication Data

US 2021/0267726 A1 Sep. 2, 2021

Related U.S. Application Data

(63) Continuation-in-part of application No. 16/716,105, filed on Dec. 16, 2019.

(30) Foreign Application Priority Data

Jun. 25, 2019 (TW) .................. 108122116
Sep. 30, 2020 (TW) .................. 109134171

(51) Int. Cl.
*A61C 8/00* (2006.01)
*A61B 6/00* (2006.01)
(Continued)

(52) U.S. Cl.
CPC .............. *A61C 8/005* (2013.01); *A61B 6/032* (2013.01); *A61B 6/14* (2013.01); *A61B 6/4085* (2013.01);
(Continued)

(58) Field of Classification Search
CPC ....... A61C 8/005; A61C 8/0045; A61C 8/008; A61C 9/0046; A61C 13/0004; A61C 13/00; A61B 6/032; A61B 6/14; A61B 6/4085
See application file for complete search history.

(56) References Cited

U.S. PATENT DOCUMENTS

2015/0025855 A1* 1/2015 Fisker ................... A61C 9/004
703/1

FOREIGN PATENT DOCUMENTS

| KR | 1469833 B1 * | 12/2014 | ........... A61C 8/0022 |
| TW | I686182 B | 3/2020 | |
| WO | WO2013/112233 * | 9/2014 | ............... A61B 1/24 |

OTHER PUBLICATIONS

Exocad ("exocad Video Tutorial (basic): Custom Abutment Design", 2017) (Year: 2017).*

(Continued)

*Primary Examiner* — Xin Sheng
(74) *Attorney, Agent, or Firm* — Hamre, Schumann, Mueller & Larson, P.C.

(57) ABSTRACT

A method for producing an adaptive element for dental implantation includes: creating a 3D virtual model including a crown part and a root part; obtaining a boundary curve between the crown part and the root part; defining a boundary plane on the root part perpendicular to a vertical axis of the 3D virtual model and spaced apart from the boundary curve; projecting the boundary curve on the boundary plane in a direction parallel to the vertical axis; generating a tubular model having a predetermined thickness based on the boundary curve, a virtual surface connected from the boundary curve to the cutting plane, and the cutting plane; and producing the adaptive element according to the tubular model.

10 Claims, 12 Drawing Sheets

(51) Int. Cl.
    *A61B 6/03*         (2006.01)
    *A61B 6/14*         (2006.01)
    *A61C 9/00*         (2006.01)
    *A61C 13/00*        (2006.01)

(52) U.S. Cl.
    CPC ............ *A61C 8/0045* (2013.01); *A61C 8/008* (2013.01); *A61C 9/0046* (2013.01); *A61C 13/0004* (2013.01); *A61C 13/0019* (2013.01)

(56) References Cited

OTHER PUBLICATIONS

Mangano et al ("A novel full-digital protocol (SCAN-PLAN-MAKE-DONE®) for the design and fabrication of implant-supported monolithic translucent zirconia crowns cemented on customized hybrid abutments." International Journal of Environmental Research and Public Health 16.3 (2019): 317 (Year: 2019).*
Organical ("Exocad 3D Printing Files", Jun. 4, 2019) (Year: 2019).*
ExocadBrochure ("The complete software solution for digital dentistry", 2015) (Year: 2015).*
Search Report appended to an Office Action, which was issued to Taiwanese counterpart application No. 109134171 by the TIPO dated Jun. 8, 2021, with an English translation thereof (2 pages).

\* cited by examiner

METHOD OF PRODUCING ADAPTIVE ELEMENT FOR DENTAL IMPLANTATION

CROSS-REFERENCE TO RELATED APPLICATION

This application is a continuation-in-part of U.S. patent application Ser. No. 16/716,105, filed on Dec. 16, 2019, which claims priority of Taiwanese Invention Patent Application No. 108122116 filed on Jun. 25, 2019. This application further claims priority of Taiwanese Invention Patent Application No. 109134171, filed on Sep. 30, 2020.

FIELD

The disclosure relates to dental implantation, and more particularly to an adaptive element for dental implantation.

BACKGROUND

In conventional dental implantation, a first stage is to bury an implant, which is a metal post serving as a tooth root, in a patient's jaw bone by surgery.

After 3 to 6 months of osseointegration, the implant may become permanently stable, meaning that new bone has grown to the surface of the implant. Then, an abutment is attached to the implant for securing a dental crown (or prosthetic tooth). Lastly, the dental crown is connected to the abutment with lag screws or with dental cement.

In general, conventional abutments are designed to have standardized sizes and shapes. A dentist can only select one that matches the buried implant and most suitably fits the patient's gum. However, the fit may not be perfect so the selected conventional abutment may be too tight or too loose for the gum.

SUMMARY

Therefore, an object of the disclosure is to provide a method for producing an adaptive element for dental implantation that can alleviate at least one of the drawbacks of the prior art.

According to the disclosure, the method includes steps of:
creating, by a model creating equipment, a three-dimensional (3D) virtual model of a target tooth of a patient, the 3D virtual model including a crown part and a root part connected to the crown part;
obtaining, by a processing device, a boundary curve between the crown part and the root part on the 3D virtual model;
defining, by the processing device, a boundary plane on the root part of the 3D virtual model in a manner that the boundary plane is perpendicular to a vertical axis of the 3D virtual model and is spaced apart from the boundary curve;
projecting, by the processing device, the boundary curve on the boundary plane in a direction parallel to the vertical axis;
generating, by the processing device, a tubular model having a predetermined thickness based on the boundary curve, a virtual surface connected from the boundary curve to the cutting plane, and the cutting plane; and
producing, by a 3D forming equipment, the adaptive element according to the tubular model.

BRIEF DESCRIPTION OF THE DRAWINGS

Other features and advantages of the disclosure will become apparent in the following detailed description of the embodiment(s) with reference to the accompanying drawings, of which.

DETAILED DESCRIPTION

Figure 1:
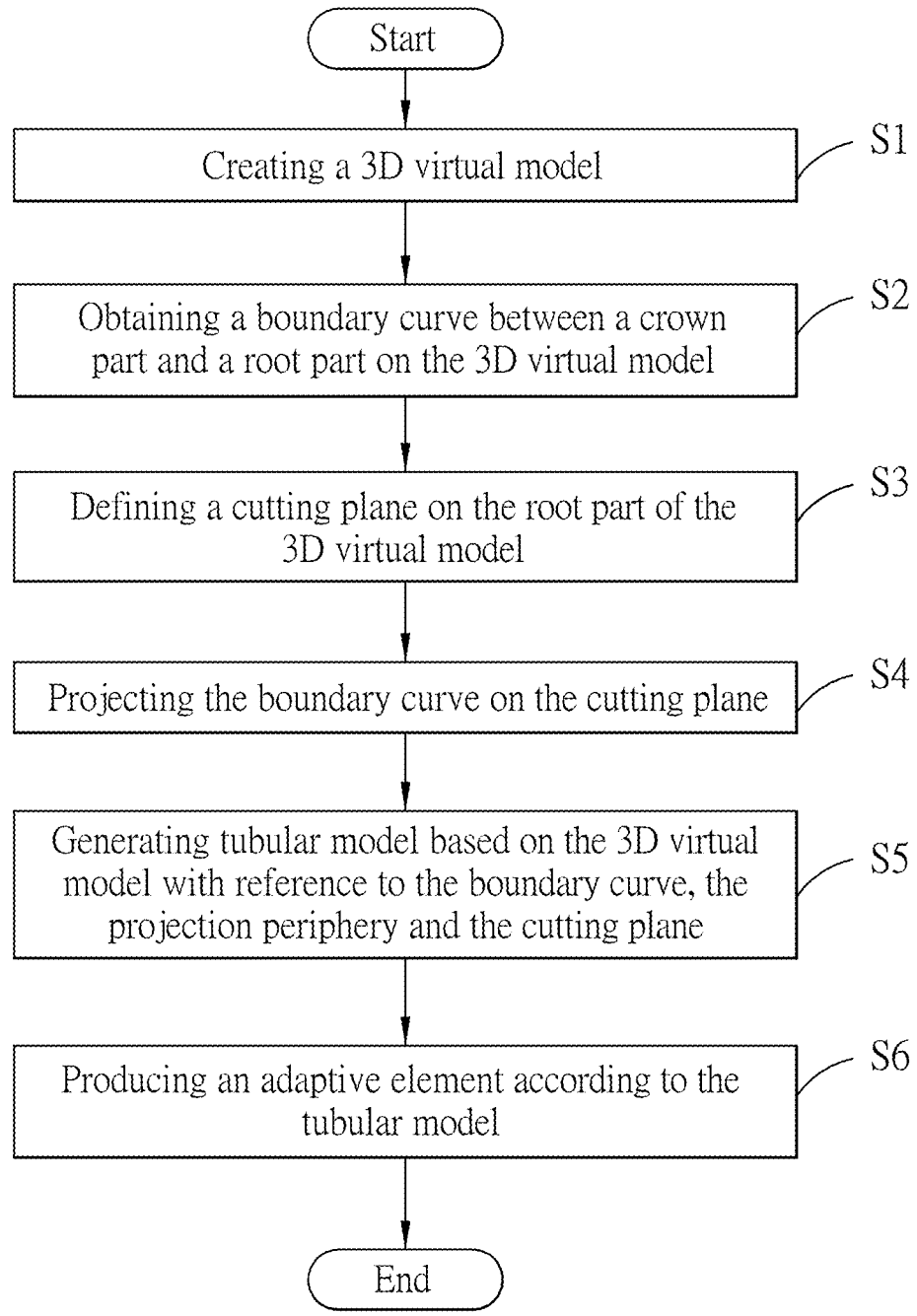
FIG. 1 is a flow chart exemplarily illustrating a method for producing an adaptive element for dental implantation according to an embodiment of the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Figure 12:
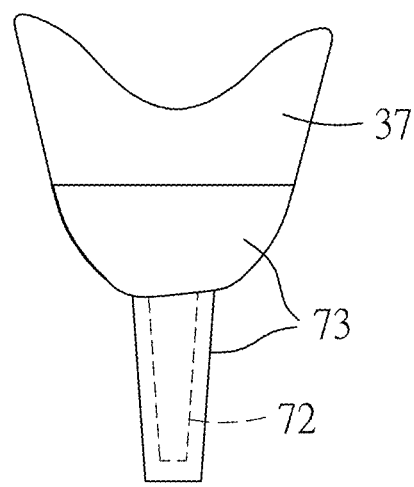
FIG. 12 is a schematic view of the integrated body that has been processed to have a smooth outer surface.
Figure 13:
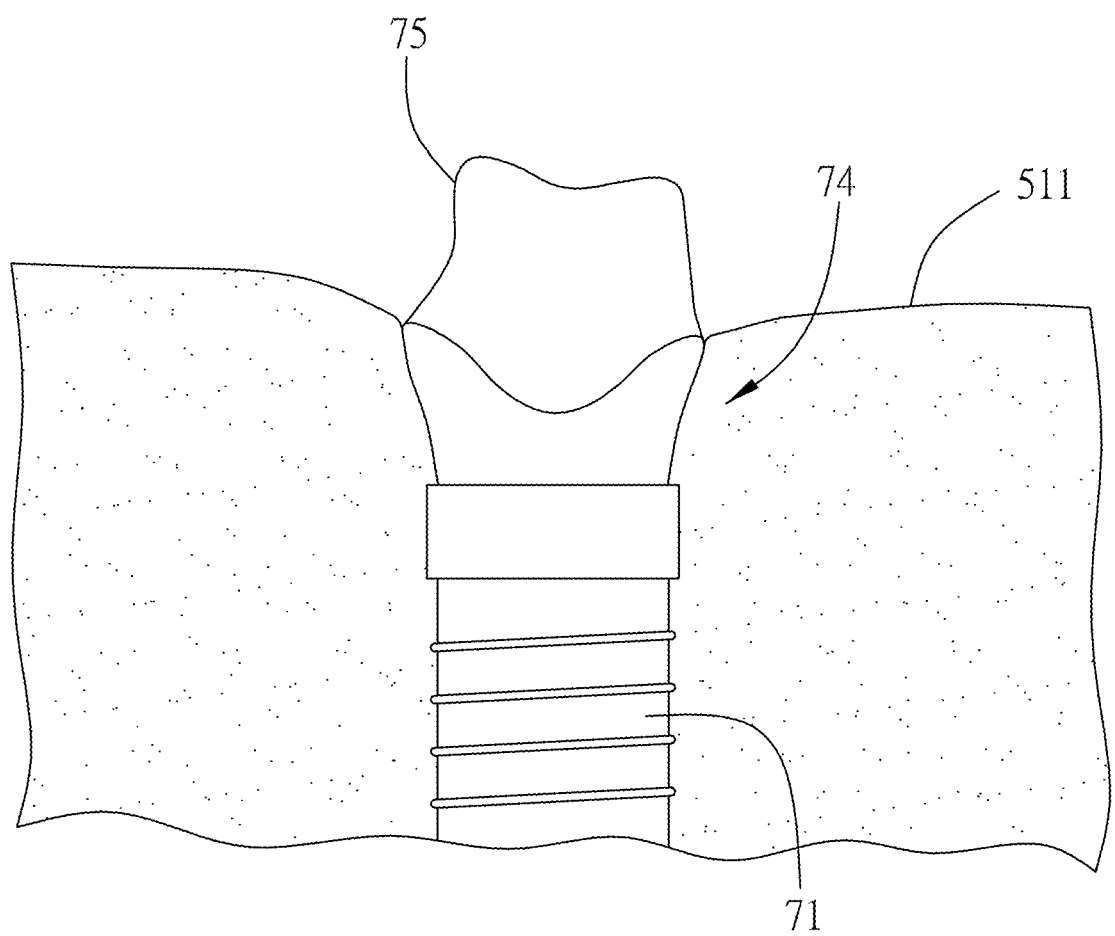
FIG. 13 is a side schematic view illustrating a dental abutment attached to an implant and securing a dental crown.

Referring to FIG. 1, a method for producing an adaptive element 37 (see FIG. 12) for dental implantation includes the steps as follows. The method is implemented by, for example, a system shown in FIG. 14. The system of FIG. 14 includes a model creating equipment 11, a processing device 12 and a three-dimensional (3D) forming equipment 13.

Figure 2:
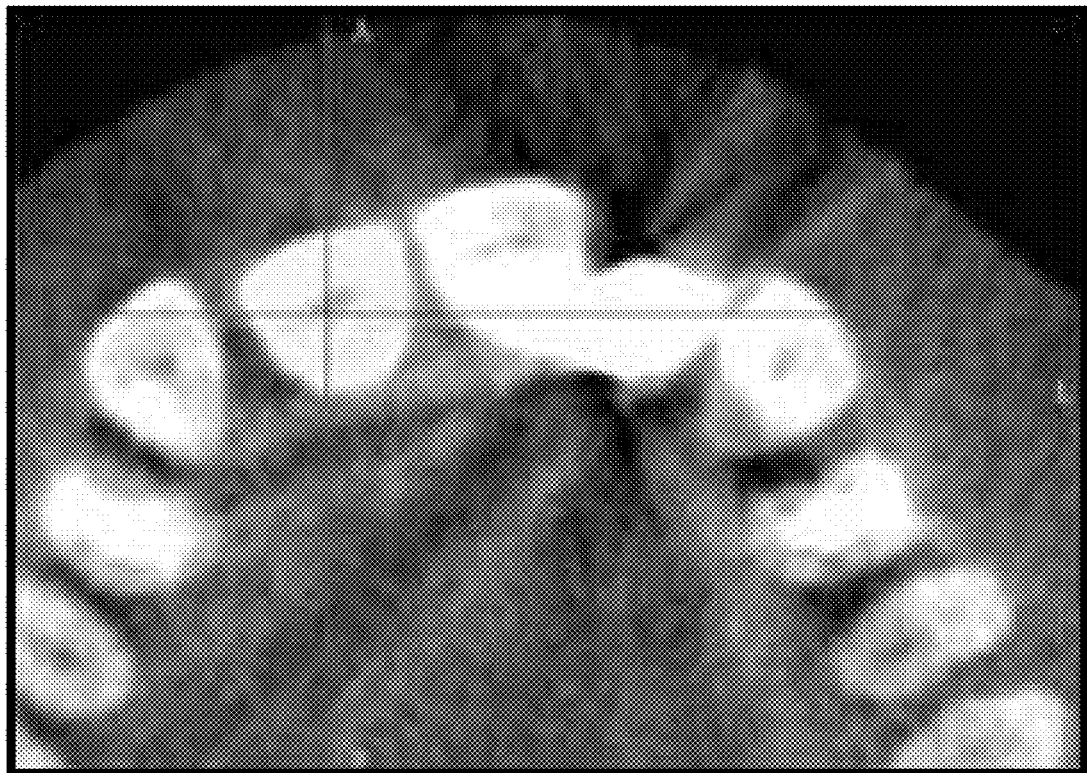
FIG. 2 is an axial view of a target tooth of a patient.
Figure 3:
FIG. 3 is a sagittal view of the target tooth of the patient.
Figure 4:
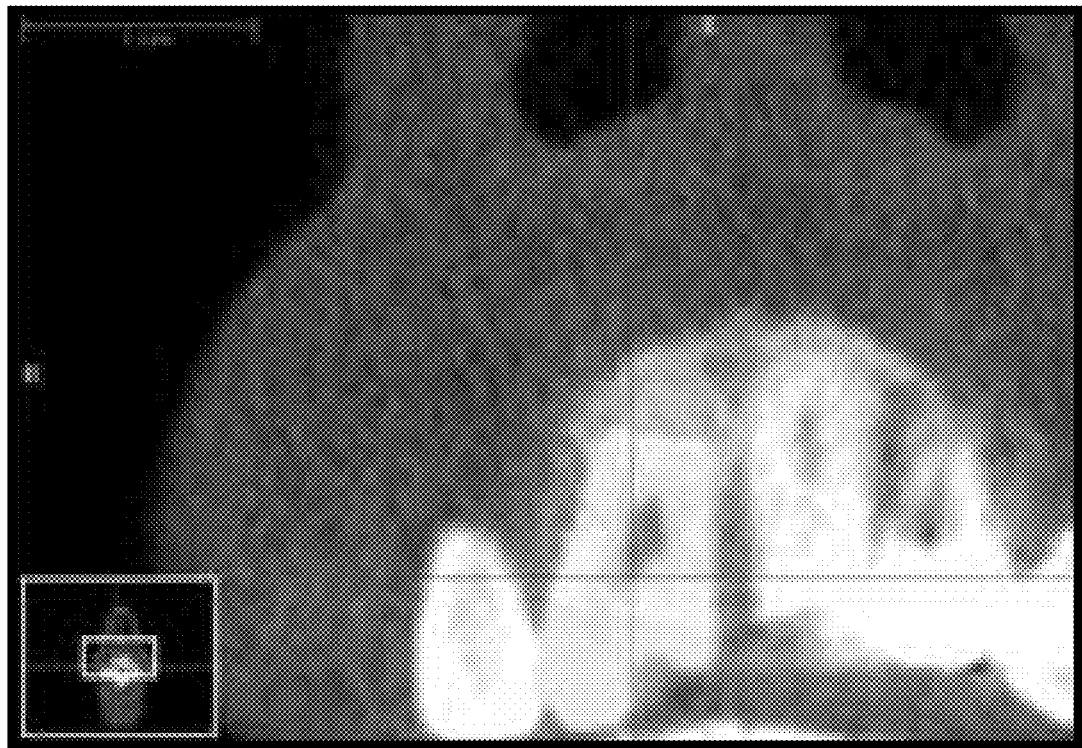
FIG. 4 is a coronal view of the target tooth of the patient.
Figure 6:
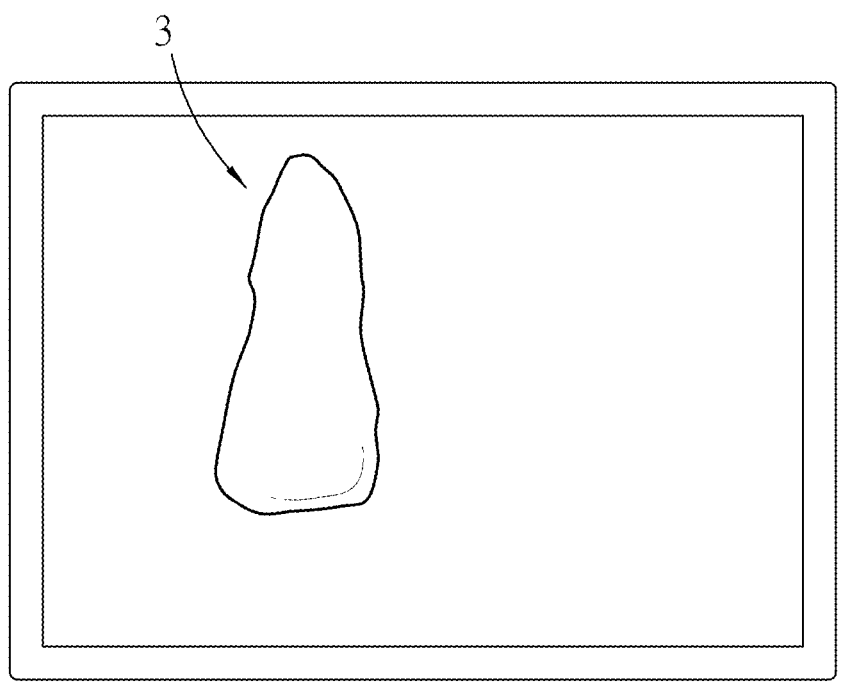
FIG. 6 is a schematic view of a three-dimensional (3D) virtual model.
Figure 7:
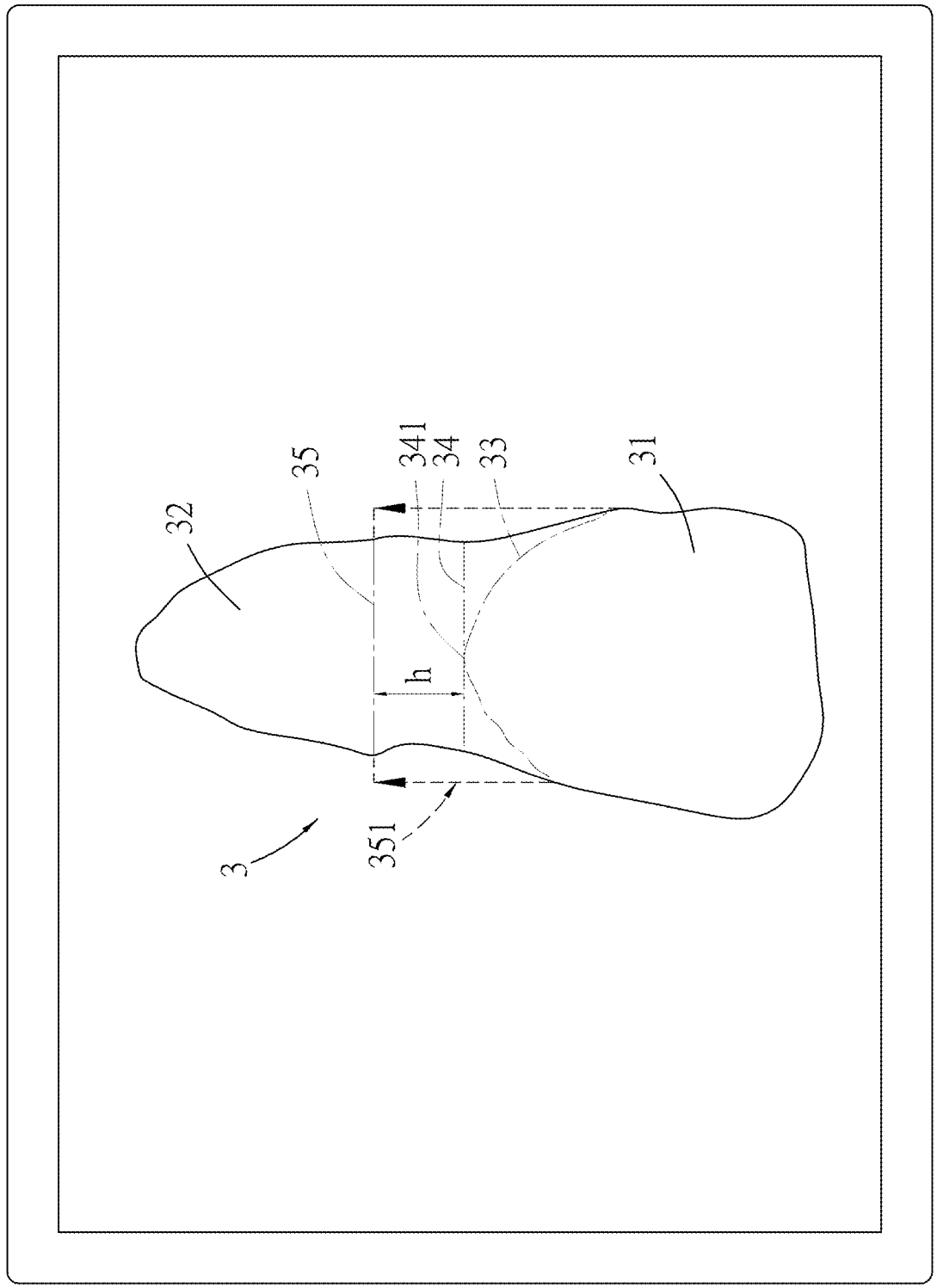
FIG. 7 is a schematic view illustrating a boundary curve between a crown part and a root part of the 3D virtual model, and a boundary plane that is defined with reference to the boundary curve.

In step S1 of the method, the model creating equipment 11 creates a 3D virtual model 3 (see FIGS. 6 and 7) of a target tooth of a patient. According to the embodiment, the model creating equipment 11 includes a scanning device 111 (e.g., a cone beam computed tomography (CBCT) system), and an image processor 112. The scanning device 111 obtains 3D images of the target tooth as shown in FIGS. 2 to 4. The image processor 112 receives the images from the scanning device 111 and creates the 3D virtual model 3 based thereon. The image processor 112 is, for example, a computer having a non-transitory memory storing an image processing software (e.g., ITK-snap or OsiriX, etc.), and a processing module (e.g., an integrated circuit chip, a programmable logic device, a Programmable Gate Array (PGA), a field-programmable gate array (FPGA), an Application Specific Integrated Circuit (ASIC), etc.) configured to execute the software.

In other embodiments, the model creating equipment 11 may be an intraoral scanner (not shown) which captures digital impressions and directly creates the 3D virtual model 3 according to the digital impressions thus captured. In further other embodiments, the model creating equipment 11 may be a conventional 3D scanner (not shown) that is used to create the 3D virtual model 3 based on a physical tooth model, which is obtained by conventional impression techniques.

Figure 5:
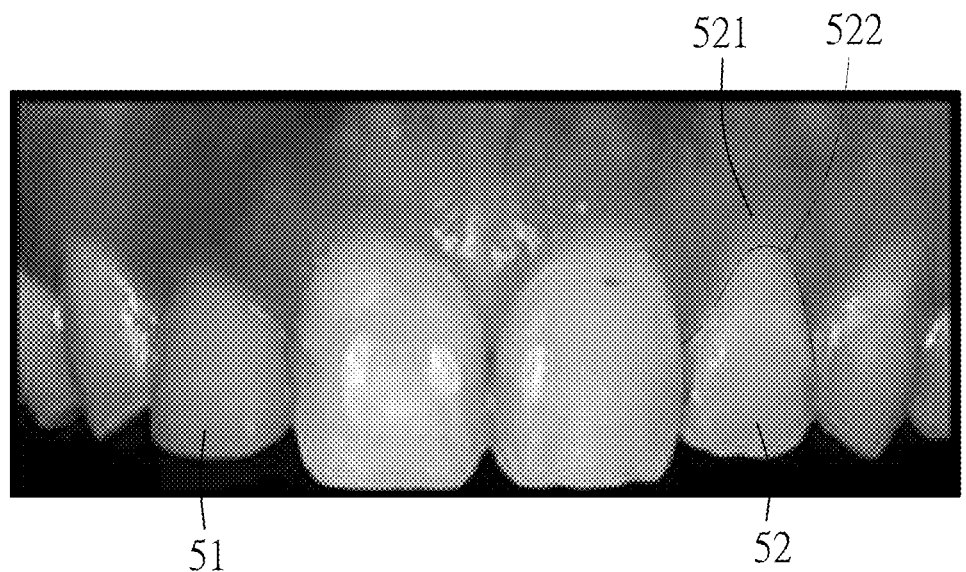
FIG. 5 is a picture showing a to-be-treated tooth on one side and a symmetric tooth on the other side.

Further referring to FIG. 5, the target tooth may be a to-be-treated tooth 51, or a symmetric tooth 52 that is located on the other side of the mouth, symmetrically to the to-be-treated tooth 51. Specifically, when the to-be-treated tooth 51 has a complete root, the to-be-treated tooth 51 may be designated as the target tooth even if the crown thereof has decayed or damaged. Alternatively, when the root of the to-be-treated tooth 51 has decayed or damaged or there is a missing tooth, the symmetric tooth 52 of the to-be-treated tooth 51 or the missing tooth may be designated as the target tooth.

The 3D virtual model 3 includes a crown part 31 and a root part 32 connected to the crown part 31. Specifically, the crown part 31 and the root part 32 of the 3D virtual model 3 correspond to a crown and a root of the to-be-treated tooth 51 or the missing tooth, respectively.

It should be noted that, in the case that the symmetric tooth 52 is designated as the target tooth, the image processor 112 initially creates an initial 3D model that corresponds to and represents the symmetric tooth 52 based on the images of the target tooth, and then creates a mirrored copy of the initial 3D model to serve as the 3D virtual model 3 that corresponds to the to-be-treated tooth 51 or the missing tooth.

In step S2, the processing device 12 obtains a boundary curve 33 between the crown part 31 and the root part 32 on the 3D virtual model 3. The boundary curve 33 corresponds to a boundary 522 (see FIG. 5) between, for example, the symmetric tooth 52 and a gum part 521 of the gums. In some embodiments, the image processor 112 may serve as the processing device 12.

In one embodiment, the processing device 12 analyzes variation of the curvature of a facial surface of the 3D virtual model 3 to obtain the boundary curve 33 according to the variation of the curvature. It should be noted that the facial surface means the labial side for an anterior tooth (e.g., incisors and canines), and means the buccal side of a posterior tooth (e.g., molars and premolars). In some embodiments, an operator may manually mark a plurality of points between the crown part 31 and the root part 32 on the 3D virtual model 3, and the processing device 12 then connects the marked points to obtain the boundary curve 33 or constructs the boundary curve 33 that has the best fit to the marked points.

In step S3, the processing device 12 defines a boundary plane 35 on the root part 32 of the 3D virtual model 3 in a manner that the boundary plane 35 is spaced apart from the boundary curve 33 and is perpendicular to a vertical axis of the 3D virtual model 3. The vertical axis is defined in the coronal and apical directions of the tooth represented by the 3D virtual model 3. In one embodiment, the processing device 12 defines, as the boundary plane 35, a plane that is parallel to and spaced apart by a predetermined distance (h) from a tangent plane 34 touching a reference point 341 of the boundary curve 33 and perpendicular to the vertical axis, wherein the reference point 341 is an extremity of the boundary curve 33 on the facial surface of the 3D virtual model 3 in a direction parallel to the vertical axis. The predetermined distance (h) may be 3 mm, and may be adjusted on demand.

In step S4, the processing device 12 projects the boundary curve 33 on the boundary plane 35 in the direction parallel to the vertical axis. A virtual surrounding surface extending from the boundary curve 33 to the boundary plane 35 is defined as a projection periphery 351.

Figure 8:
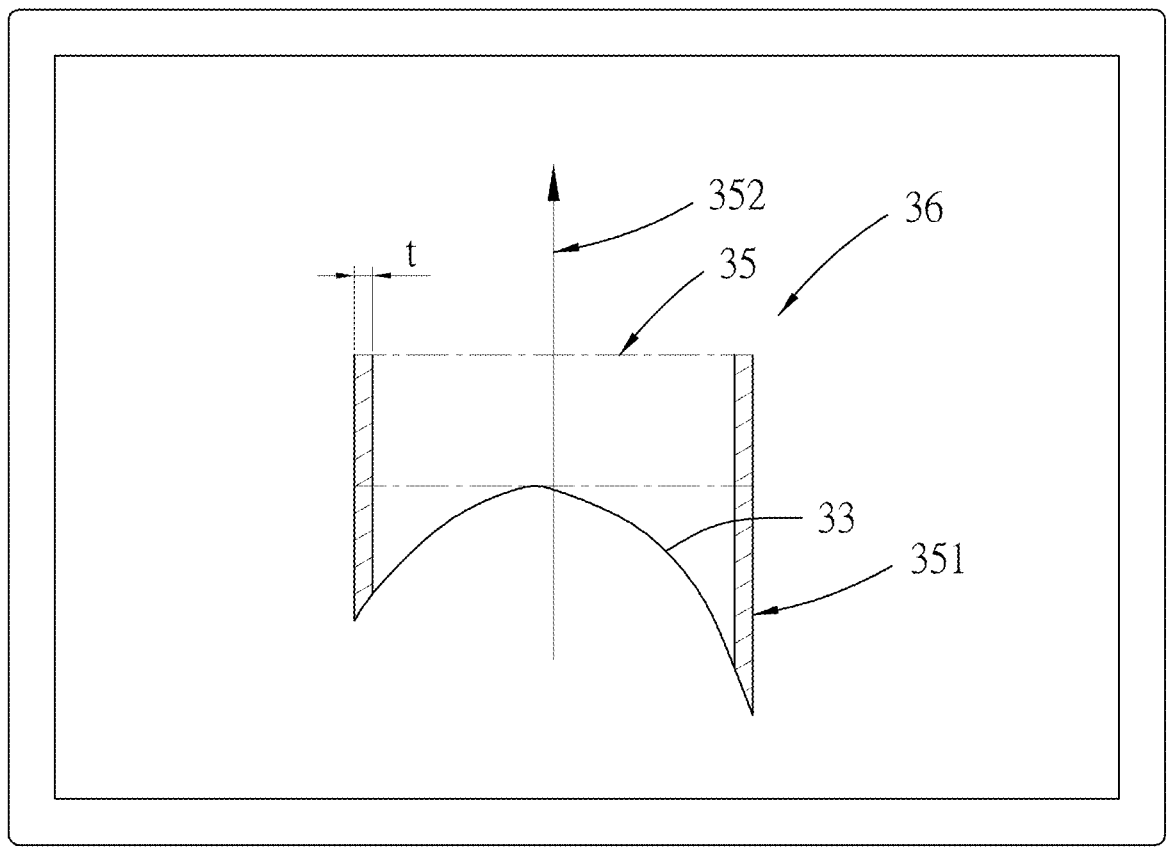
FIG. 8 is a schematic view of a tubular model generated based on the 3D virtual model.

In step S5, the processing device 12 generates a tubular model 36 (see FIG. 8) based on the boundary curve 33, the projection periphery 351 and the boundary plane 35. Specifically, the tubular model 36 is created based on the projection periphery 351 that defines a surrounding wall surrounding a central axis 352 of the tubular model 36, the boundary plane 35 that defines an opening end of the tubular model 36, and the boundary curve 33 that defines the other opening end of the tubular model 36.

The surrounding wall of the tubular model 36 has a predetermined thickness (t). In general, the predetermined thickness (t) may be preset to be 0.8~1 mm, but not limited thereto.

Figure 9:
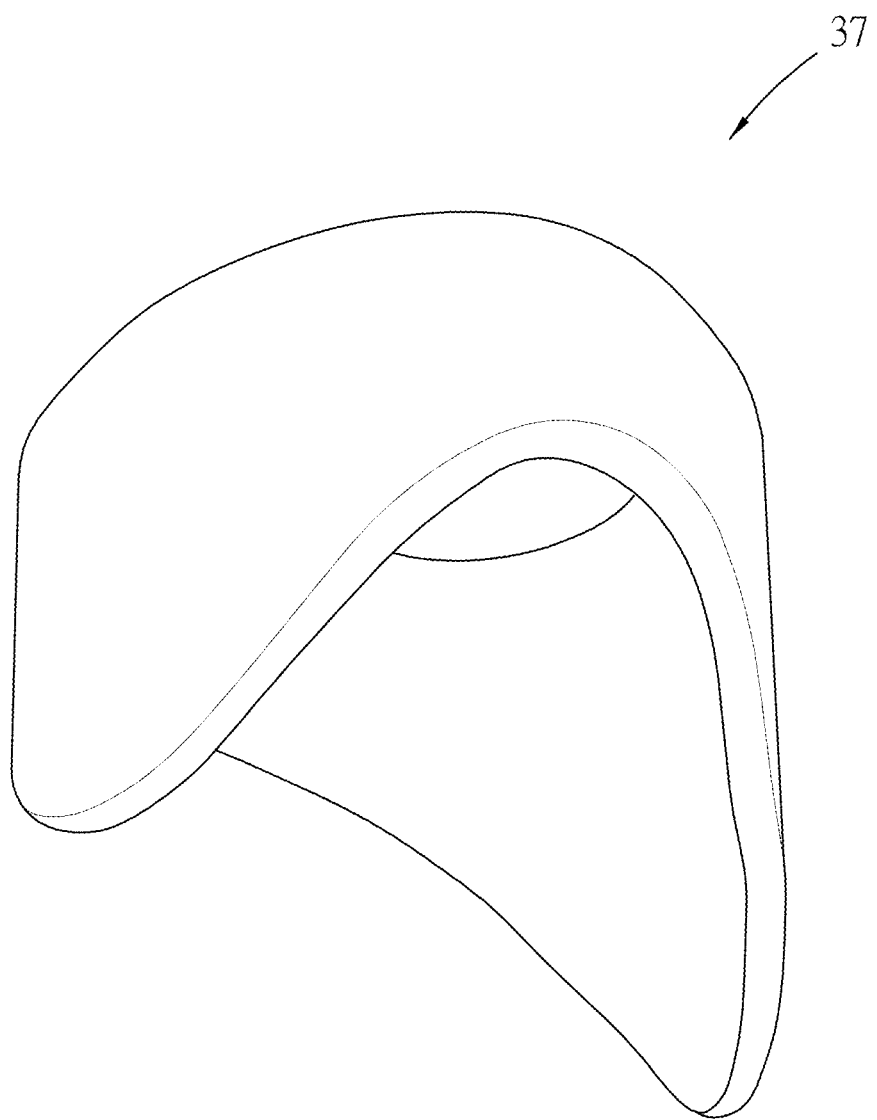
FIG. 9 is a schematic view of an adaptive element for dental implantation produced based on the tubular model.

In step S6, the 3D forming equipment 13, which may be a 3D printer, a turning process machine, or a molding machine, produces the adaptive element 37 (see FIG. 9) for dental implantation based on the tubular model 36. Then, the adaptive element 37 could be used in the dental implantation process.

Figure 10:
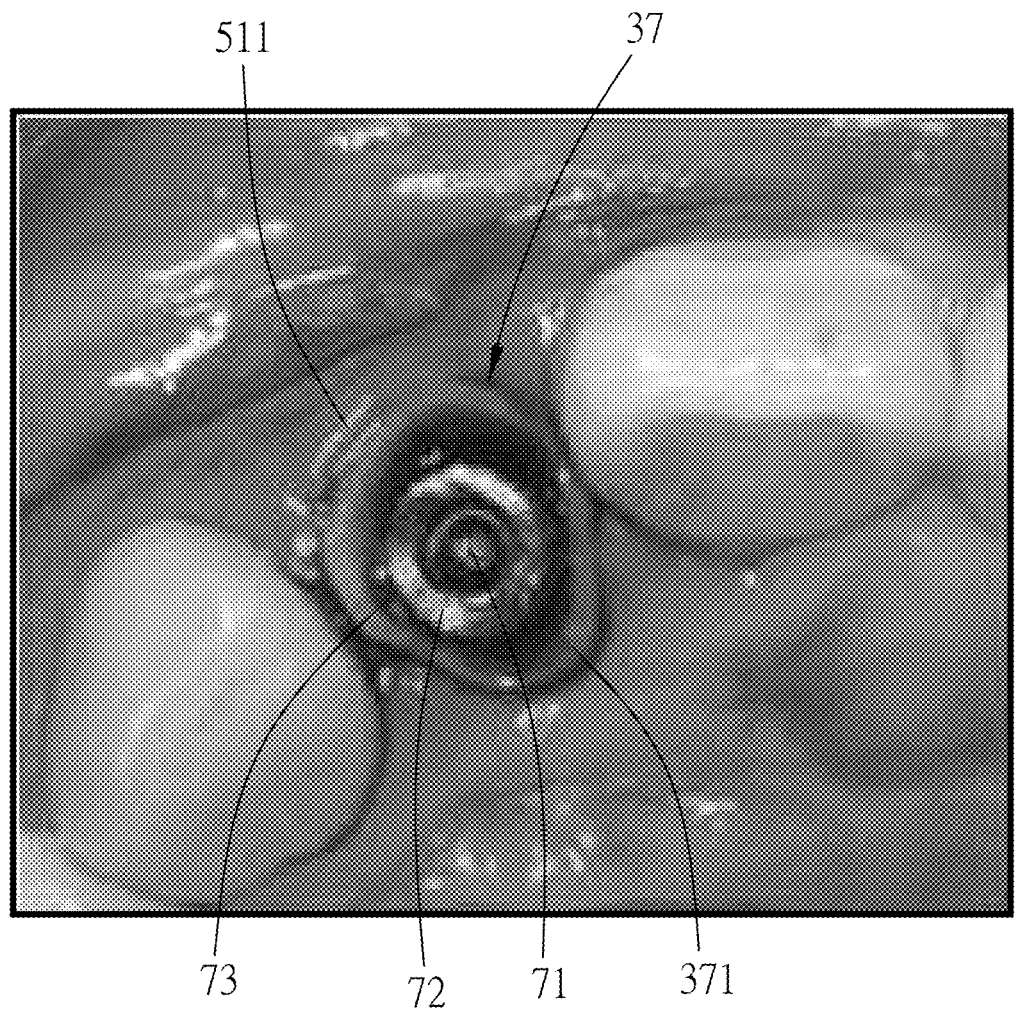
FIG. 10 is a photo showing the adaptive element applied in a dental implantation process.
Figure 11:
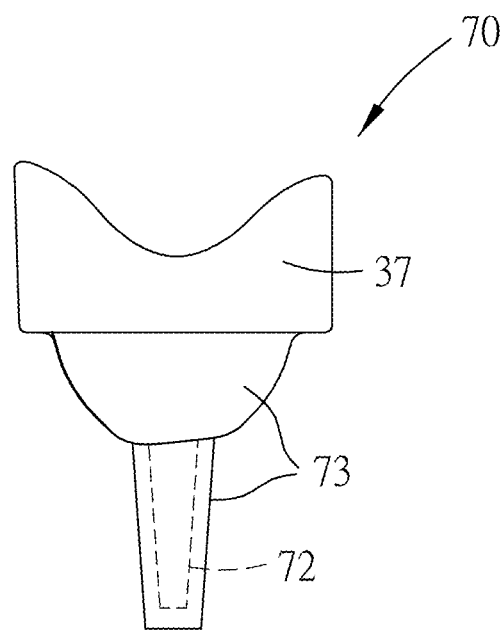
FIG. 11 is a schematic view of an integrated body composed by the adaptive element, a temporary abutment and resin.

Referring to FIGS. 10 and 11, when the to-be-treated tooth 51 has been taken out by a dentist or when the patient is missing a tooth, a dental implant 71 may be interfaced with (implanted and bonded with) the jawbone of the patient. A temporary abutment 72 is then selected by the dentist and then mounted onto the implant 71. Next, the adaptive element 37 is placed into a hole in a gum part 511 of the gums where the to-be-treated tooth 51 was originally rooted or that corresponds to an original location of the missing tooth, to surround the temporary abutment 72 and to support an inner wall of the hole. Since the adaptive element 37 is customized according to the boundary curve 33, which corresponds to the boundary between the crown and the root of the target tooth, the adaptive element 37 will ideally be a perfect fit for the edge of the hole in the patient's gums. The dentist then fills up the space between the temporary abutment 72 and the adaptive element 37 with resin 73 so as to integrate the temporary abutment 72 and the adaptive element 37 to form an integrated body 70. The integrated body 70 is thus composed by the temporary abutment 72, the adaptive element 37 and the resin 73.

After the resin 73 rigidifies, the dentist dismounts the integrated body 70. The integrated body 70 may be processed to remove a stage between the adaptive element 37 and the resin 73. Accordingly, the integrated body 70 that has been processed would have a smooth outer surface corresponding to the adaptive element 37 and a part of the resin 73 (see FIG. 12). Then, a dental abutment 74 may be produced based on the integrated body 70 that has been processed. In some embodiments, the dental abutment 74 may be made of metal or zirconia and produced by a 3D printer, a turning process machine, or a molding machine.

Figure 14:
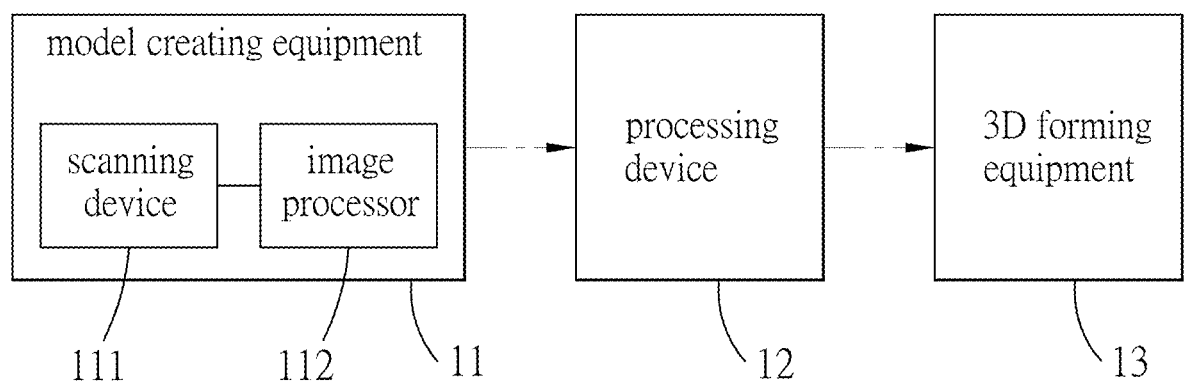
FIG. 14 is a block diagram exemplarily illustrating components of a system according to an embodiment of this disclosure.

Lastly, as shown in FIG. 14, the dental abutment 74 is mounted on the implant 71, and a crown 75 is then bonded to the dental abutment 74 by cementing or screwing.

As described above, in the embodiments of the present invention, a 3D virtual model 6 is constructed based on 3D images of a to-be-treated tooth 51 or a symmetric tooth 52 of the patient, a tubular model 67 is obtained from the 3D virtual model 6, and an adaptive element 37 for dental implantation is then produced according to the tubular model 67. Thus, the adaptive element 37 may be applied during dental implantation and the dental abutment 74 may be produced accordingly. Since the part of the dental abutment 74 which is mounted to the gums is produced according to the adaptive element 37, it may fit the hole in the gum part 511 of the patient very well. Further, since the stage between the adaptive element 37 and the resin 73 of the integrated body 70 has been removed (see FIGS. 11 and 12), there will be a space between the inner wall of the hole in the gum part 511 and the dental abutment 74 that is made based on the integrated body 70 mounted on the implant 71, allowing the gum part 511 to grow so as to fit the dental abutment 74 properly.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A method for producing an adaptive element for dental implantation, comprising steps of:
    creating, by a model creating equipment, a three-dimensional (3D) virtual model of a target tooth of a patient, the 3D virtual model including a crown part and a root part connected to the crown part, the target tooth being a to-be-treated tooth on a side of the patient's mouth, or a symmetric tooth located on another side of the patient's mouth;
    obtaining, by a processing device, a boundary curve between the crown part and the root part on the 3D virtual model of the target tooth;
    defining, by the processing device, a boundary plane on the root part of the 3D virtual model of the target tooth in a manner that the boundary plane is perpendicular to a vertical axis of the 3D virtual model and is spaced apart from the boundary curve;
    projecting, by the processing device, the boundary curve on the boundary plane in a direction parallel to the vertical axis;
    generating, by the processing device, a tubular model having a predetermined thickness based on the boundary curve, a virtual surface connected from the boundary curve to the boundary plane, and the boundary plane; and
    producing, by a 3D forming equipment, the adaptive element according to the tubular model,
    wherein the step of defining the boundary plane includes:
    defining, as the boundary plane, a plane that is parallel to and spaced apart by a predetermined distance (h) from a tangent line touching a reference point of the boundary curve and that is perpendicular to the vertical axis, wherein the reference point is an extremity of the boundary curve of the 3D virtual model;
    wherein the virtual surface connected from the boundary curve to the boundary plane is defined as a projection periphery;
    wherein, in the step of generating the tubular model, the tubular model is created based on the projection periphery that defines a surrounding wall surrounding a central axis of the tubular model, the boundary plane that defines an opening end of the tubular model, and the boundary curve that defines another opening end of the tubular model.

2. The method as claimed in claim 1, wherein the step of generating a tubular model is to generate the tubular model to have the predetermined thickness in a range of 0.8 mm to 1 mm.

3. The method as claimed in claim 1, wherein the step of creating a 3D virtual model includes creating an initial 3D model of the target tooth based on images of the target tooth, and creating a mirrored copy of the initial 3D model to serve as the 3D virtual model.

4. The method as claimed in claim 1, wherein the step of creating a 3D virtual model includes obtaining images of a target tooth by a cone beam computed tomography (CBCT) system, and creating the 3D virtual model based on the images.

5. The method as claimed in claim 1, wherein the step of creating a 3D virtual model includes capturing digital impressions and creating the 3D virtual model according to the digital impressions.

6. The method as claimed in claim 1, wherein the step of generating a tubular model includes generating the tubular model to have the predetermined thickness (t) of 0.8 mm to 1 mm.

7. The method as claimed in claim 1, wherein the step of producing the adaptive element includes producing the adaptive element using one of a 3D printer, a turning process machine, and a molding machine.

8. A method for producing a dental abutment based on an adaptive element produced by the method of claim 1, comprising:
    interfacing a dental implant with a jawbone of the patient;
    mounting a temporary abutment on the dental implant interfaced with the jawbone of the patient;
    placing the adaptive element into a hole in gums of the patient where a to-be-treated tooth of the patient was originally embedded, to surround the temporary abutment that has been mounted on the dental implant interfaced with the jawbone of the patient,
    filling up the space between the temporary abutment and the adaptive element with resin so as to integrate the temporary abutment and the adaptive element to form an integrated body;
    dismounting the integrated body from the dental implant; and
    producing the dental abutment based on the integrated body.

9. The method as claimed in claim 8, wherein the step of producing the dental abutment includes:
   processing the integrated body to remove a stage between the adaptive element and the resin, so as to make the integrated body have a smooth outer surface corresponding to the adaptive element and a part of the resin; and
   producing the dental abutment based on the integrated body that has been processed.

10. The method of claim 1, wherein the tubular model has predetermined parameters corresponding to the target tooth.

* * * * *